United States Patent [19]

Toder

[11] Patent Number: 4,760,146

[45] Date of Patent: * Jul. 26, 1988

[54] CYCLOHEXENE CARBOXYLIC ESTERS AND AMIDES AS ANTIDYSRHYTHMIC AGENTS

[75] Inventor: Bruce H. Toder, Rochester, N.Y.

[73] Assignee: Pennwalt Corporation, Philadelphia, Pa.

[*] Notice: The portion of the term of this patent subsequent to Jun. 17, 2003 has been disclaimed.

[21] Appl. No.: 830,592

[22] Filed: Feb. 18, 1986

[51] Int. Cl.⁴ .................. C07D 295/14; C07C 103/19; C07C 103/737; C07C 69/75

[52] U.S. Cl. .................................... 546/234; 546/239; 540/610; 544/58.1; 544/165; 544/169; 544/172; 544/399; 544/400; 548/567; 548/573; 560/37; 564/164

[58] Field of Search ............... 546/234, 239; 540/610; 560/37; 564/164; 548/567, 573; 544/169, 172, 399, 400, 165, 58.1

[56] References Cited

U.S. PATENT DOCUMENTS

| | | | |
|---|---|---|---|
| 3,557,127 | 1/1971 | Satzinger | 546/239 |
| 3,951,978 | 4/1976 | Manghisi et al. | 546/239 |
| 3,974,157 | 8/1976 | Shetty et al. | 546/239 |
| 4,452,745 | 6/1984 | Lacefield et al. | 564/164 |
| 4,595,759 | 6/1986 | Davidson et al. | 564/164 |

*Primary Examiner*—Norma S. Milestone
*Attorney, Agent, or Firm*—Panitch, Schwarze, Jacobs and Nadel

[57] ABSTRACT

Novel compounds and processes for making and using them. The compounds include ethyl 1-[3-(1-piperidinyl)propyl]-6-phenyl-3-cyclohexene-1-carboxylate, 1-[3-(1-piperidinyl)propyl]-6-phenyl-3-cyclohexene-1-carboxyamide, and N,N-dimethyl-1-[3-(1-piperidinyl)propyl]-6-phenyl-3-cyclohexene-1-carboxamide.

6 Claims, No Drawings

CYCLOHEXENE CARBOXYLIC ESTERS AND AMIDES AS ANTIDYSRHYTHMIC AGENTS

INTRODUCTION AND BACKGROUND

The present invention provides a novel class of cyclohexene esters and amides thereof that are useful as antidysrhythmic agents. While the art teaches cyclohexane compounds structurally, as in U.S. Pat. No. 3,974,157 and British Patent No. 615,136, it does not, to Applicant's knowledge, teach analogs bearing a carboxy ester or amide group on the number one carbon of the cyclohexane ring or analogues with a site of unsaturation within the cyclohexane ring.

BRIEF SUMMARY OF THE INVENTION

The compounds of the invention are those of the formula I

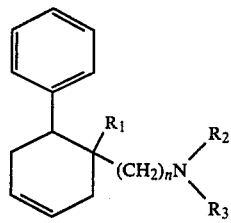

(I)

wherein
$R_1$ is $C_1-C_4$ alkyl carboxylate or

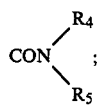

$R_2$ and $R_3$ are either independently hydrogen, $C_3-C_7$ cycloalkyl or $C_1-C_4$ alkyl, or $R_2$ and $R_3$ taken together with the adjacent nitrogen atom forms a 5-7 membered saturated heterocyclic ring containing 4-6 carbon atoms and 1-2 heteroatoms chosen from N, O, or S;

$R_4$ and $R_5$ are independently hydrogen, $C_1-C_4$ alkyl or $C_4-C_7$ cycloalkyl; and n is 2 or 3, including all racemic, optically active and stereoisomeric forms, thereof, and including all pharmaceutically acceptable salts thereof.

The invention is also processes for making the compounds of the invention and their use as antidysrhythmic agents.

DETAILED DESCRIPTION OF THE INVENTION

Preferred compounds are those of formula I in which: $R_1$ is $C_1-C_3$ alkyl carboxylate, $R_2$ and $R_3$ are either independently hydrogen or $C_1-C_3$ alkyl or $R_2$ and $R_3$ taken together with the adjacent nitrogen atom form a saturated heterocyclic ring containing one nitrogen atom and 4 to 5 carbon atoms; $R_4$ and $R_5$ are independently H or $C_1-C_3$ alkyl; and n is 2 or 3.

Being organic bases, the compounds of this invention readily form salts with organic and inorganic acids such as hydrochloric, sulfuric, maleic, tartaric, and other non-toxic acids to form pharmaceutically acceptable acid addition salts.

Alkyl groups may be straight or branched chains.

PROCESS FOR PRODUCTION

The compounds of this invention can be prepared in several ways. In schemes A and B, below, $R_2$, $R_3$, $R_4$ and $R_5$ are as defined above, R is $C_1-C_4$ alkyl, and Ar is phenyl.

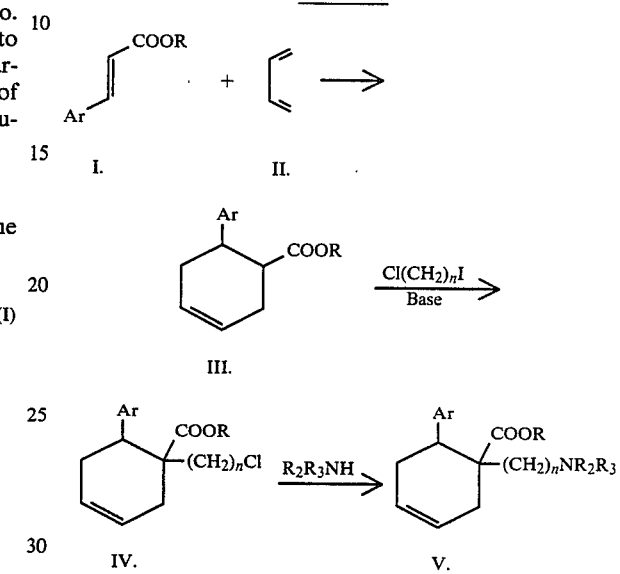

In scheme A, structure I is selected from β-phenyl acrylic acid esters such as methyl cinnamate, ethyl cinnamate, propyl cinnamate, or butyl cinnamate and reacted with butadiene (II) to form the corresponding 6-phenyl-3-cyclohexene-1-carboxylic acid ester (III). Treatment of this ester with ω-chloroalkyliodide in the presence of base yields the corresponding 1-(ω-chloroalkyl)-6-phenyl-3-cyclohexene-1-carboxylic acid ester (IV). Amine displacement of the halide affords the corresponding compound of the invention (V).

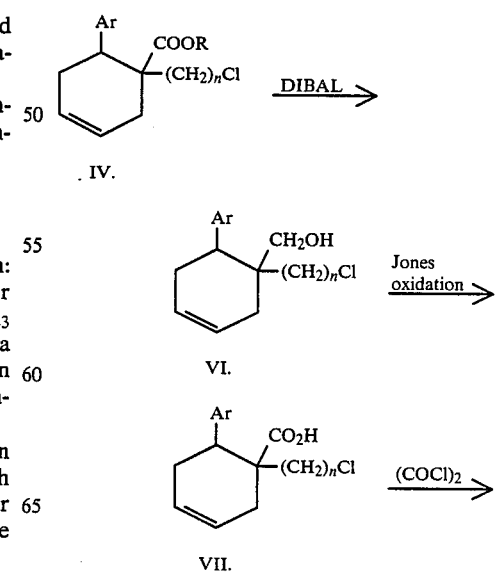

-continued
Scheme B

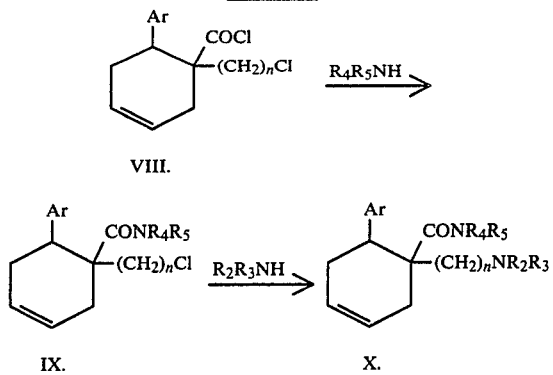

In Scheme B, the ester (IV) is reduced to a primary alcohol (VI) upon reaction with diisobutylaluminum hydride (DIBAL). Jones oxidation ($CrO_3/H_2SO_4$) of the alcohol VI affords 1-(ω-chloroalkyl)-6-phenyl-3-cyclohexene-1-carboxylic acid (VII). Conversion of the acid (VII) to the corresponding acid chloride (VIII) proceeds utilizing oxalyl chloride. Selective reaction of an amine represented by $R_4R_5NH$ with the acid chloride (VIII) in a non-polar solvent yields an amide (IX). Chloride displacement with an amine $R_2R_3NH$ in a polar solvent at elevated temperature affords the desired compound of the invention (X).

In Schemes A and B, the amines represented by $R_2R_3NH$ can be selected from methylamine, ethylamine, propylamine, isopropylamine, butylamine, t-butylamine, cyclopropylamine, cyclobutylamine, cyclopentylamine, cyclohexylamine, cycloheptylamine, pyrrolidine, piperidine, morpholine, hexamethyleneimine, 1-methylpiperazine, thiomorpholine and the like and reacted to give the corresponding structures V and X. $R_4R_5NH$ can be selected from ammonia, methylamine, ethylamine, propylamine, isopropylamine, butylamine, isobutylamine, dimethylamine, diethylamine, butylethylamine, cyclobutylamine, cyclopentylamine, cyclohexylamine, cycloheptylamine, and the like. By appropriate combinations of the intermediates and reagents of Schemes A and B compounds of formula I may be prepared.

The following are representative of the compounds that may be prepared:
ethyl-1-[3-(methylamino)propyl]-6-phenyl-3-cyclohexene-1-carboxylate,
ethyl-1-[2-(diisopropylamino)ethyl]-6-phenyl-3-cyclohexene-1-carboxylate,
ethyl-1-[3-(cyclopentylamino)propyl]-6-phenyl-3-cyclohexene-1-carboxylate,
ethyl-1-[2-(4-morpholinyl)ethyl]-6-phenyl-3-cyclohexene-1-carboxylate,
ethyl-1-[3-(1-pyrrolidinyl)propyl]-6-phenyl-3-cyclohexene-1-carboxylate,
1-[2-ethylamino)ethyl]-6-phenyl-3-cyclohexene-1-carboxamide,
1-[3-(dimethylamino)propyl]-6-phenyl-3-cyclohexene-1-carboxamide,
1-[2-(di-t-butylamino)ethyl]-6-phenyl-3-cyclohexene-1-carboxamide,
1-[3-(cyclopropylamino)propyl]-6-phenyl-3-cyclohexene-1-carboxamide,
1-[3-(1-piperidinyl)ethyl]-6-phenyl-3-cyclohexene-1-carboxamide,
N-methyl-1-[3-(butylamino)propyl]-6-phenyl-3-cyclohexene-1-carboxamide,
N-methyl-1-[2-(dipropylamino)ethyl]-6-phenyl-3-cyclohexene-1-carboxamide,
N-propyl-1-[3-(cycloheptylamino)propyl]-6-phenyl-3-cyclohexene-1-carboxamide,
N-butyl-1-[3-(4-morpholinyl)propyl]-6-phenyl-3-cyclohexene-1-carboxamide,
N,N-diethyl-1-[2-(methylamino)ethyl]-6-phenyl-3-cyclohexene-1-carboxamide,
N,N-diisopropyl-1-[3-(diisopropylamino)propyl]-6-phenyl-3-cyclohexene-1-carboxamide,
N,N-dibutyl-1-[2-(cyclobutylamino)ethyl]-6-phenyl-3-cyclohexene-1-carboxamide,
N,N-dimethyl-1-[2-(1-pyrrolidinyl)ethyl]-6-phenyl-3-cyclohexene-1-carboxamide.

The invention is more specifically illustrated by the following examples which are representative of the invention but are not intended to limit the scope of the invention.

EXAMPLE 1

Preparation of ethyl 1-[3-(1-piperidinyl)propyl]-6-phenyl-3-cyclohexene-1-carboxylate Ethyl 1-(3-chloropropyl)-6-phenyl-3-cyclohexene-1-carboxylate Ethyl cinnamate (1 mol, 176 g), hydroquinone (3 g), copper powder (8 g), and butadiene (280 ml) were mixed with benzene (350 ml). The reaction mixture was heated in a bomb at 210° C. for 6 hrs. The reaction mixture waas allowed to cool. The contents were concentrated in vacuo and the crude material was distilled. The fraction distilled at 111°–118° C./0.1 mm was shown by chromatography and NMR spectroscopy to be greater than 95% pure and having the structure ethyl-6-phenyl-3-cyclohexene-1-carboxylate.

A solution of lithium diisopropylamide (LDA), prepared at 0° C. under a nitrogen ($N_2$) atmosphere from diisopropylamine (0.311 mol, 31.4 g) and n-butyllithium (0.311 mol, 2.7M, 115.3 ml) using tetrahydrofuran (400 ml) as solvent, was cooled to $-78°$ C. employing a dry ice/acetone slurry. Ethyl 6-phenyl-3-cyclohexene-1-carboxylate (0.283 mol, 65 g) dissolved in tetrahydrofuran (100 ml) was added to the solution. After 45 min., 1-chloro-3-iodopropane (0.311 mol, 63.5 g) dissolved in tetrahydrofuran (50 ml) was added dropwise over the period of 30 min. The contents were allowed to warm to room temperature, whereupon 300 ml of water is added and the mixture was extracted three times with 200 ml of ethyl ether. The combined organic extracts were washed with 10% aqueous sodium thiosulfate and brine and dried over magnesium sulfate ($MgSO_4$). Upon filtration, the filtrate was concentrated in vacuo to afford a yellow oil which is distilled (155°–160° C./0.05 mm) to afford ethyl-1-(3-chloropropyl)-6-phenyl-3-cyclohexene-1-carboxylate (66.75 g, 77% yield).

Ethyl 1-[3-(1-piperidinyl)propyl]-6-phenyl-3-cyclohexene-1-carboxylate

Ethyl 1-(3-chloropropyl)-6-phenyl-3-cyclohexene-1-carboxylate (6.35 g, 20.7 mmol) was dissolved in 50 ml of dimethylformamide (DMF) to which piperidine (10 equiv, 15 ml) was added. The contents were stirred under $N_2$ at 50° C. for 16 hrs. The reaction was allowed to cool to ambient temperature, whereupon the DMF was removed on the rotovap at 3 mm pressure. To the residue was added 200 ml of ethyl ether and the organic material was washed three times with 100 ml of water. The organic fraction was dried over MgSO$_4$, filtered and concentrated in vacuo to afford after distillation (155°–160° C./0.1 mm) ethyl 1-[3-(1-piperidinyl)propyl]-6-phenyl-3-cyclohexene-1-carboxylate as a clear viscous oil (6.61 g, 90% yield).

EXAMPLE 2

Preparation of 1-[3-(1-piperidinyl)propyl]-6-phenyl-3-cyclohexene-1-carboxamide 1-(3-chloropropyl)-6-phenyl-3-cyclohexene-1-carboxylic acid Ethyl 1-(3-chloropropyl)-6-phenyl-3-cyclohexene-1-carboxylate (8.65 g, 29.4 mmol) dissolved in toluene (200 ml) was added dropwise to a 1.0M stock solution of diisobutylaluminum hydride (DIBAL, 2.2 equiv., 64.6 ml). The contents were stirred for 16 hrs. under N$_2$ at ambient temperature. The reaction was then chilled to 0° C. and water (100 ml) added. The resulting precipitate was filtered off and the filtrate was dried over MgSO$_4$, filtered, and concentrated in vacuo to afford 7.21 g (92% yield) of 1-(3-chloropropyl)-6-phenyl-3-cyclohexene-1-methanol as a clear mobile oil. Infrared spectroscopy indicated the disappearance of an ester carbonyl band and the appearance of hydroxyl stretching between 3200–3400 cm$^{-1}$. To this alcohol (27 mmol) dissolved in acetone (100 ml) and cooled to 0° C. was added Jones reagent (2.67M, 2.0 equiv., 20.3 ml). The contents were stirred for 2 hr. at which time isopropyl alcohol (20 ml) was added to quench unreacted Jones reagent. The solution was concentrated in vacuo. The residue was washed with water and extracted three times with 100 ml of ethyl ether. The combined organic extracts were dried over MgSO$_4$, filtered through celite and concentrated in vacuo to afford 1-(3-chloropropyl)-6-phenyl-3-cyclohexene-1-carboxylic acid (4.95 g, 87% yield) as a clear viscous oil. Infrared spectroscopy indicated the appearance of the carboxyl stretch at 1700 cm$^{-1}$.

1-[3-(1-piperidinyl)propyl]-6-phenyl-3-cyclohexene-1-carboxamide 1-(3-chloropropyl)-6-phenyl-3-cyclohexane-1-carboxylic acid (4.95 g, 17.6 mmol) was dissolved in methylene chloride and stirred under N$_2$ at ambient temperature. Oxalyl chloride (2 equiv., 4.47 g) was added and the solution was allowed to stir for 16 hrs. The solution was concentrated to vacuo to afford the corresponding acid chloride (5.18 g, 100% yield) as a light yellow mobile oil. The infrared spectrum indicated the disappearance of the carboxyl carbonyl stretch of the starting material at 1700 cm$^{-1}$ and the appearance of the acid chloride carbonyl stretch at 1790 cm$^{-1}$. 1-(3-Chloropropyl)-6-phenyl-3-cyclohexene-1-carbonyl chloride (11.40 g, 38.6 mmol) was dissolved in methylene chloride (100 ml) into which ammonia is bubbled into the solution for 15 mins. via a gas dispersion tube. After stirring for 16 hrs. water was added to the solution and the organic fraction was dried over MgSO$_4$, filtered and concentrated in vacuo to afford 9.05 g (85% yield) of 1-(3-chloro-propyl)-6-phenyl-3-cyclohexene-1-carboxamide as a viscous oil.

The primary amide (8.05 g, 29 mmol) was dissolved in DMF (50 ml) to which 20 ml of piperidine (excess) was added and the contents stirred at 50° C. under N$_2$ for two days. The solution was concentrated in vacuo at 3 mm pressure. The resulting oil was dissolved in ethyl ether and washed with 2.5N aqueous HCl. The organic fraction was discarded. The aqueous phase was washed with 2.5N aqueous NaOH and extracted with ethyl ether. The combined organic fractions were dried over MgSO$_4$, filtered and concentrated in vacuo to afford 4.37 g (58% yield) of 1-[3-(1-piperidinyl)propyl]-6-phenyl-3-cyclohexene-1-carboxamide as a tan solid, mp 121°–122° C.

EXAMPLE 3

Preparation of N-Methyl-1-[3-(1-piperidinyl)propyl]-6-phenyl-3-cyclohexene-1-carboxamide 1-(3-chloropropyl)-6-phenyl-3-cyclohexene-1-carbonyl chloride (7.21 g, 24.3 mmol) was dissolved in methylene chloride (100 ml). At 0° C., methylamine was bubbled into the stirring solution through a gas dispersion tube for 15 mins. and then allowed to stir for 4 hr. The solution was washed with water. The organic fraction was dried over MgSO$_4$, filtered, and concentrated in vacuo to afford 7.01 g of N-methyl-1-(3-chloropropyl)-6-phenyl-3-cyclohexene-1-carboxamide as a clear viscous oil. The infrared spectrum had a carbonyl band at 1670 cm$^{-1}$, indicative of an amide, which replaced the band for the acid chloride at 1790 cm$^{-1}$.

The secondary amide obtained above (6.95 g, 22.9 mmol) was treated with piperidine (20 ml, excess) in DMF (50 ml). The contents were stirred at 50° C. under N$_2$ for two days. The solution was concentrated in vacuo at 3 mm pressure. The resulting oil was dissolved in ethyl ether and washed with 2.5N aqueous HCl. The organic fraction was discarded. The aqueous phase was washed with 2.5N aqueous NaOH and extracted with ethyl ether. The combined organic fractions were dried over MgSO$_4$., filtered and concentrated to afford 6.45 g of a dark yellow oil. Flash chromatography, using 10% MeOH/CHCl$_3$ as eluent, afforded 2.54 g of N-methyl-1-[3-(1-piperidinyl)propyl]-6-phenyl-3-cyclohexene-1-carboxamide as a tan solid, mp 145°–147° C.

EXAMPLE 4

Preparation of N,N-Dimethyl-1-[3-(1-piperidinyl)propyl]-6-phenyl-3-cyclohexene-1-carboxamide 1-(3-chloropropyl)-6-phenyl-3-cyclohexene-1-carbonyl chloride (5.22 g, 17.5 mmol) was treated with excess dimethylamine (10 g) in methylene chloride (100 ml) to afford 4.84 g (90% yield) of N,N-dimethyl-1-(3-chloropropyl)-6-phenyl-3-cyclohexene-1-carboxamide as a viscous oil. The infrared spectrum had a carbonyl stretching frequency at 1660 cm$^{-1}$ indicative of an amide which replaced the carbonyl stretch at 1790 cm$^{-1}$ for the acid chloride. The tertiary amide isolated above (4.80 g, 15.1 mmol) was dissolved in DMF (25 ml) to which 10 ml of piperidine (excess) was added and the contents stirred at 50° C. under N$_2$ for two days. The solution was concentrated in vacuo at 3 mm pressure. The resulting oil was dissolved in ethyl ether and washed with 2.5N aqueous HCl. The organic fraction was discarded. The aqueous phase was washed with 2.5N aqueous NaOH and extracted with ethyl ether. The combined organic fractions were dried over MgSO$_4$, filtered and concentrated in vacuo to afford 5.38 g of a dark yellow viscous oil. Flash chromatography, employing 10% MeOH/CHCl$_3$, as eluent, afforded 1.95 g of N,N-dimethyl-1-[3-(1-piperidinyl)- propyl]-6-phenyl-3-cyclohexene-1-carboxamide as a tan solid, mp 105°–106° C.

UTILITY

The compounds of this invention have antidysrhythmic activity in warm-blooded animals, including humans. The antidisrhythmic activity of a compound is manifested by its ability to reverse oubain-induced arrhythmias and can be demonstrated as follows:

An anesthetized dog is prepared for recording systemic arterial blood pressure and lead II ECG. After a 30 minute stabilization period, a primary dose of 50 μg/kg (iv) ouabian is given. At 15 min. intervals an additional increment of 10 μg/kg ouabain are given until other ventricular tachycardia or multifocal ectopic arrhythmias are obtained. Test compound is then administered, usually in the range 1 to 30 mg/kg (iv), and the ECG is monitored for changes indicative of reversal of the arrhythmias. As antidisrhythmic activity will vary from compound to compound, each compound should be tested at 1, 3, 10 and 30 mg/kg to determine the minimum effective dose.

Alternatives to the intravenous route of administration are the oral, intramuscular, subcutaneous, and intraperitoneal routes, it being understood that the daily dose will have to be adjusted to the needs of the warm-blooded animal being treated.

At the time of filing this application, the inventor considers the compound of Example 1, ethyl 1-[3-(1-piperidinyl)propyl]-6-phenyl-3-cyclohexene-1-carboxylate, to be the preferred compound of the invention as regards antidysrhythmic activity.

What is claimed is:

1. A compound of formula I

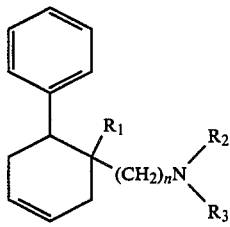

(I)

wherein $R_1$ is $C_1$–$C_4$ alkyl carboxylate or

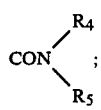

$R_2$ and $R_3$ are either independently hydrogen, $C_3$–$C_7$ cycloalkyl or $C_1$–$C_4$ alkyl, or $R_2$ and $R_3$ taken together with the adjacent nitrogen atom forms pyrrolidino, piperidino, morpholino, hexamethyleneimino, 1-methylpiperazino, or thiomorpholino;

$R_4$ and $R_5$ are independently hydrogen, $C_1$–$C_4$ alkyl or $C_4$–$C_7$ cycloalkyl; and n is 2 or 3, or a pharmaceutically acceptable salt thereof.

2. A compound of claim 1 in which: $R_1$ is $C_1$–$C_3$ alkyl carboxylate; $R_2$ and $R_3$ are either independently hydrogen or $C_1$–$C_3$ alkyl, or $R_2$ and $R_3$ taken together with the adjacent nitrogen atom form pyrrolidino or piperidino; $R_4$ and $R_5$ are independently H or $C_1$–$C_3$ alkyl; and n is 2 or 3.

3. A compound of claim 1 in which $R_2$ and $R_3$ together with the adjacent nitrogen atom form piperidino, $R_1$ is

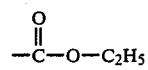

and n is 3.

4. A compound of claim 1 in which $R_2$ and $R_3$ together with the adjacent nitrogen atom form piperidino, $R_1$ is

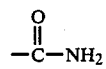

and n is 3.

5. A compound of claim 1 in which $R_2$ and $R_3$ together with the adjacent nitrogen atoms form piperidino, $R_1$ is

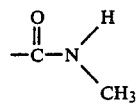

and n is 3.

6. A compound of claim 1 in which $R_2$ and $R_3$ together with the adjacent nitrogen atom form piperidino, $R_1$ is

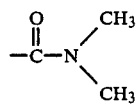

and n is 3.

* * * * *